United States Patent
Albrecht et al.

[11] 4,001,402
[45] Jan. 4, 1977

[54] CARDENOLIDE GLYCOSIDES AND METHOD OF MAKING THE SAME, AND THERAPEUTIC COMPOSITION

[75] Inventors: Hans Peter Albrecht, Luetzelsachsen ueber Weinheim; Guenter Neugebauer, Mannheim, both of Germany

[73] Assignee: Knoll A.G. Chemische Fabriken, Ludwigshafen (Rhine), Germany

[22] Filed: Apr. 5, 1976

[21] Appl. No.: 673,592

[30] Foreign Application Priority Data

Apr. 18, 1975 Germany .................... 2517293

[52] U.S. Cl. .................... 424/182; 536/7
[51] Int. Cl.² .................... A61K 31/705
[58] Field of Search ........... 260/210.5; 424/182

[56] References Cited
UNITED STATES PATENTS

| | | | |
|---|---|---|---|
| 3,472,836 | 10/1969 | Vogelsang et al. | 260/210.5 |
| 3,963,697 | 6/1976 | Coombes | 424/182 |

*Primary Examiner*—Lewis Gotts
*Assistant Examiner*—Cary Owens
*Attorney, Agent, or Firm*—Curtis, Morris & Safford

[57] ABSTRACT

Cardioactive glycosides of the formula

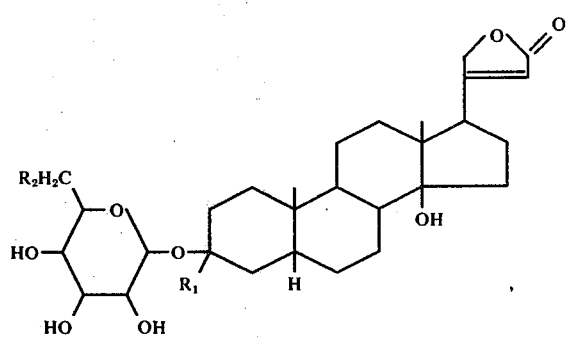

are disclosed, wherein $R_1$ is saturated aliphatic hydrocarbon having 1 – 4 carbon atoms or unsaturated aliphatic hydrocarbon having 2 – 4 carbon atoms or phenyl and $R_2$ is hydrogen or hydroxyl, as are methods for making the same by reacting the corresponding aglycone with an acylated 1-halo-hexopyranose of the formula

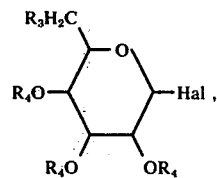

wherein Hal is halogen, $R_3$ is hydrogen or alkanoyloxy having 1 – 4 carbon atoms, and $R_4$ is alkanoyl having 1 – 4 carbon atoms or benzoyl, and subsequently cleaving the acyl groups.

8 Claims, No Drawings

CARDENOLIDE GLYCOSIDES AND METHOD OF MAKING THE SAME, AND THERAPEUTIC COMPOSITION

The present invention relates to cardenolide glycosides, to a method for making the same, and to pharmaceutical compositions containing these compounds.

The cardiac glycosides used therapeutically and known for some time in the art are derived from steroids of the cardenolide series or of the bufadienolide series which contain a secondary β-hydroxy group on the carbon in the 3-position. The steroidal aglycone is, in the corresponding glycoside, bound to a mono-, di-, tri-, or tetra-saccharide group by way of the oxygen atom of this hydroxy group. Despite considerable differences in their pharmacokinetic behavior, a very small therapeutic ratio, which makes their practical utilization difficult, is common to all compounds of these classes.

It has now been found that glycosides which are derived from cardenolides having a tertiary hydroxy group in the 3-position exhibit a greater therapeutic ratio in comparison to the cardiac glycosides heretofore known.

The present invention relates more in particular to novel cardioactive glycosides of the formula

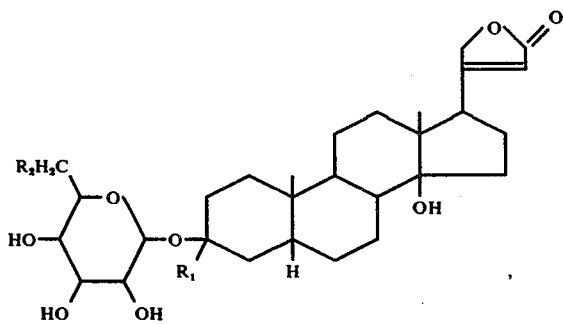

wherein $R_1$ is a saturated aliphatic hydrocarbon group having 1 – 4 carbon atoms or is an unsaturated aliphatic hydrocarbon group having 2 – 4 carbon atoms, or is phenyl, and $R_2$ is hydrogen or hydroxy.

The invention further relates more in particular to a process for making compounds of the formula given above by reacting, in the presence of an acid acceptor, an aglycone of the formula

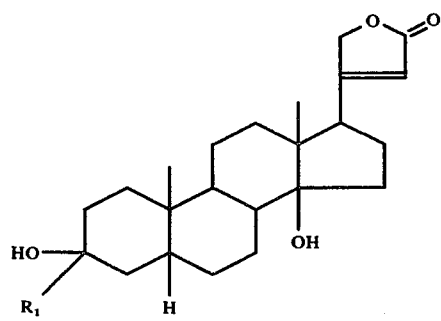

wherein $R_1$ has its earlier significance, with an acylated 1-halohexopyranose of the formula

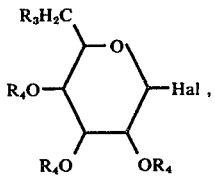

wherein Hal is halogen, $R_3$ is hydrogen or an alkanoyloxy group having 1 – 4 carbon atoms, and $R_4$ is an allkanoyl group having 1 – 4 carbon atoms or is benzoyl. After reaction, the acyl groups are cleaved by alkaline hydrolysis in the presence of a weak base.

The reaction of the steroidal aglycone of the formula given above is suitably carried out with an excess of the acylated 1-halo-hexopyranose (3 – 5 mols per mol) at room temperature in an inert solvent such as methylene chloride, dichloroethane, ether, tetrahydrofuran, dioxane, benzene, acetonitrile, or nitromethane. Among these, dichloroethane and nitromethane are preferred. As the halogenated hexopyranose, bromo and chloro compounds are preferred.

The reaction time is, as a rule, from 12 – 48 hours. As acid acceptors, silver (I) oxide, silver (I) carbonate, mercury (II) oxide, mercury (II) carbonate, mercury (II) cyanide, or cadmium carbonate can be employed. The most suitable acid acceptor is mercury (II) cyanide, used for the first time by Helferich et al. in glycoside syntheses [Chem. Ber. 89, 314 (1956); Chem. Ber. 91, 1794 (1958)].

For deacylation, weak bases such as methanolic ammonia or potassium bicarbonate in aqueous methanol are suitable. The reaction temperature is preferably from 20° – 70° C.

The reaction conditions employed in the synthesis of the invention are those usually used in sugar chemistry for the synthesis of glycosides and which are also adaptable to the synthesis of cardenolide glycosides from aglycones having secondary C-3 hydroxy groups. What is new and surprising is that it is possible to glycosidize the tertiary C-3 hydroxyl group, which has little reactivity because of steric hinderance, under conditions which lead neither to a glycosidization of a second tertiary hydroxyl group present in the molecule on the carbon atom in the 14-position nor to the notoriously very easy elimination of this group.

The therapeutic ratio of the new compounds was determined as follows: The time rate of change of the intraventricular pressure, dp/dt, in cats under urethane/chloralose was registered while continuously administering the glycoside. The maximum inotropically effective dose (MID), the arrhythmia dose (AD) and the lethal dose (LD) were respectively determined on the same animal. The ratios of these doses were used as a measure of the therapeutic ratio, arbitrarily taking the MID as unit value.

The results are shown in the following Table, in which Index 1 = AD/MID and Index 2 = LD/MID. $\tilde{X}$ is the median value among 10 to 20 measured values.

TABLE

| Compound | Index 1 | Index 2 |
|---|---|---|
| | ~ ($\tilde{X}$) | ~ ($\tilde{X}$) |
| 3-methyl-14-hydroxy-3β-(α-L-rhamnopyranosyloxy)-5β,14β-card-20(22)-enolide | 1.61 | 2.93 |

TABLE-continued

| Compound | Index 1 | Index 2 |
| --- | --- | --- |
| Digitoxin | 1.08 | 1.40 |

The Table shows that the indices for 3-methyl-14-hydroxy-3β-(α-L-rhamnopyranosyloxy)-5β,14β-card-20(22)-enolide are significantly larger than those for digitoxin. Thus, the arrhythmia dose for the compounds of the invention is approximately six times greater than for digitoxin, while the lethal dose is approximately five times greater than for digitoxin.

The compounds of the invention are administered orally for the treatment of all forms of cardiac insufficiency in the conventional dosage unit forms. The amount of active ingredient so administered is between about 0.003 and 0.3 mg/kg per day. For administration, the compounds may be combined with conventional liquid or solid excipients to form tablets, dragees, capsules, solutions, or the like.

A better understanding of the invention and of its many advantages will be had by referring to the following specific examples, given by way of illustration. In the Examples, the Rf-values were determined on silica gel plates (F 254, obtainable from Merck, Darmstadt, Germany). Methylene chloride/methanol (5:1) was used as the solvent system.

EXAMPLE 1

5.2 g (13.4 m mol) of 3β,14-dihydroxy-3-methyl-5β,14β-card-20(22)-enolide in 130 ml of anhydrous 1,2-dichloroethane are combined with 21.7 g (40.2 m mol) of 2,3,4-tri-O-benzoyl-1-bromo-α-L-rhamnopyranose, 18.0 g of mercury (II) cyanide, and 10 g of molecular sieve A 4. The materials are reacted for 24 hours at room temperature with stirring, with the exclusion of atmospheric moisture, and while conducting a light stream of nitrogen therethrough. After filtration over a filtering agent comprising diatomaceous earth of differing grain sizes (commercially available under the tradename "Celite") and subsequent washing with chloroform, the filtrate is brought to about 1000 ml with chloroform, then washed with two 150 ml portions of 20 percent aqueous potassium iodide solution and two 100 ml portions of water. The solution is then dried over sodium sulfate and evaporated.

The residue is dissolved in 100 ml of methanol and combined at 60° – 70° C., with stirring, with 2 ml of a saturated aqueous potassium bicarbonate solution. At intervals of 30 minutes, four further two ml portions of potassium bicarbonate solution are added. The progress of the reaction is determined by means of thin layer chromatography (methylene chloride/methanol 10:1). After 3 – 4 hours, the reaction is concluded. The mixture is then cooled to room temperature, combined with 900 ml of chloroform, and washed with two 50 ml portions of water. The aqueous phases are extracted with 500 ml of chloroform/methanol (10:1). All of the organic phases obtained are combined, dried over sodium sulfate, and evaporated. Chromatography of the residue using a silica gel column (elution with methylene chloride/methanol 10:1) and crystallization from methylene chloride/methanol/hexane give 3.6 g (50 percent) of 3-methyl-14-hydroxy-3β-(α-L-rhamnopyranosyloxy)-5β,14β-card-20(22)-enolide.
m.p. = 264° – 271° C.
$[\alpha]_D^{20} = -17°$ (c = 0.5, chloroform/ethanol 9:1)
UV (methanol): 217 nm (16,800)
Rf-value: 0.61
$C_{30}H_{46}O_8$ (MW = 534.7) Calculated: C = 67.39 H = 8.67 Found : C = 67.3 H = 9.1

Using a tablet press, tablets having a weight of 120 mg are prepared in conventional fashion each to contain 1.0 mg of the compound of this Example, 80.0 mg of lactose, 35.0 mg of potato starch, 3.0 mg of gelatine, and 1.0 mg of magnesium stearate.

EXAMPLE 2

7.0 g (7.7 m mol) of 3α,14-dihydroxy-3-methyl-5β,14β-card-20(22)-enolide are reacted as in Example 1 with 12.4 g (23.0 m mol) of 2,3,4-tri-O-benzoyl-1-bromo-α-L-rhamnopyranose. 2.6 g (63 percent of theory) of 3-methyl-14-hydroxy-3α-(α-L-rhamnopyranosyloxy)-5β,14β-card-20(22)-enolide are obtained.
m.p. = 165° – 172° C. (ethanol/water)
$[\alpha]_D^{20} = -18°$ (c = 0.5, methanol)
UV (methanol): 217 nm (16,700)
Rf-value: 0.61
$C_{30}H_{46}O_8$ (MW = 534.7) Calculated: C = 67.39 H = 8.67 Found : C = 67.2 H = 8.4

EXAMPLE 3

2.0 g (5.0 m mol) of 3-ethinyl-3β,14-dihydroxy-5β,14β-card-20(22)-enolide are reacted as in Example 1 with 8.1 g (15 m mol) of 2,3,4-tri-O-benzoyl-1-bromo-α-L-rhamnopyranose. 1.3 g (48 percent of theory) of 3-ethinyl-14-hydroxy-3β-(α-L-rhamnopyranosyloxy)-5β, 14β-card-20(22)-enolide are obtained.
m.p. = 263° – 280° C. (methanol/hexane)
$[\alpha]_D^{20} = -8°$ (c = 0.5, chloroform/ethanol 9:1)
UV (methanol): 217 nm (16,500)
Rf-value: 0.61
$C_{31}H_{44}O_8$ (MW = 544.7) Calculated: C = 68.36 H = 8.14 Found C = 68.3 H = 8.2

Using a tablet press, tablets having a weight of 40 mg are prepared in conventional fashion each to contain 0.5 mg of the compound of this Example, 5.0 mg of talc, 32.0 mg of cornstarch, 2.0 mg of polyvinyl pyrrolidone, and 0.5 mg of magnesium stearate.

EXAMPLE 4

2.6 g (6.5 m mol) of 3-ethinyl- 3α,14-dihydroxy-5β,14β-card-20(22)-enolide are reacted according to Example 1 with 10.6 g (19.5 m mol) of 2,3,4-tri-O-benzoyl-1-bromo-α-L-rhamnopyranose. 2.2 g (62 percent of theory) of 3-ethinyl-14-hydroxy-3α-(α-L-rhamnopyranosyloxy)-5β,14β-card-20(22)-enolide are obtained.
m.p = 165° – 167° C. (ethanol/water)
$[\alpha]_D^{20} = -19°$ (c = 0.5, chloroform)
UV (methanol): 217 nm (17,000)
Rf-value: 0.62
$C_{31}H_{44}O_8$ (MW = 544.7) Calculated: C = 68.36 H = 8.14 Found : C = 68.6 H = 8.4

EXAMPLE 5

372 mg (1 m mol) of 3β,14-dihydroxy-3-methyl-5β,14β-card-20(22)-enolide in 10 ml of dichloroethane are reacted with 2.55 g (4 m mol) of 2,3,4,6-tetra-O-acetyl-1-bromo-α-D-glucopyranose in the presence of 2.5 g of silver carbonate and 3 g of molecular sieve A 4 for 24 hours at room temperature with stirring and with exclusion of atmospheric moisture. After filtration over "Celite", the filtrate is brought to 200 ml with chloroform, washed with water, dried over sodium sulfate, and evaporated.

The residue is dissolved in methanol and combined with methanolic ammonia. The mixture is kept at room temperature for 1 hour and subsequently evaporated. The residue is chromatographed as in Example 1. 160 mg (29 percent of theory) of 3β-(β-D-glucopyranosyloxy)-14-hydroxy-3-methyl-5β,14β-card-20(22)-enolide are obtained.

m.p. = 235° – 245° C. (methylene chloride/ethanol/hexane)

$[\alpha]_D^{20} = +5°$ (c = 0.5, methanol)

UV (methanol): 217 nm (16,300)

Rf-value: 0.44

$C_{30}H_{46}O_9$ (MW = 550.7) Calculated: C =65.43 H = 8.42 Found : C = 65.2 H = 8.5

What is claimed is:

1. A cardioactive glycoside of the formula

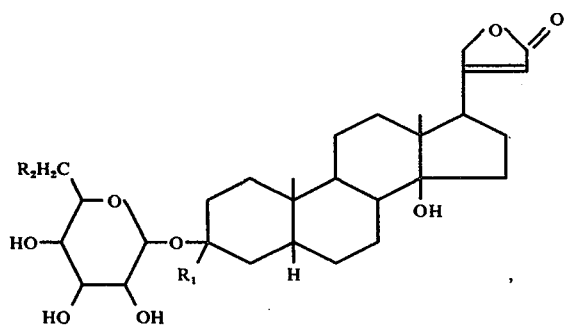

wherein $R_1$ is saturated aliphatic hydrocarbon having 1 – 4 carbon atoms or unsaturated aliphatic hydrocarbon having 2 – 4 carbon atoms or phenyl and $R_2$ is hydrogen or hydroxyl.

2. A compound as in claim 1 which is 3-methyl-14-hydroxy-3β-(α-L-rhamnopyranosyloxy)-5β,14β-card-20(22)-enolide.

3. A compound as in claim 1 which is 3-methyl-14-hydroxy-3α-(α-L-rhamnopyranosyloxy)-5β,14β-card-20(22)-enolide.

4. A compound as in claim 1 which is 3-ethinyl-14-hydroxy-3β-(α-L-rhamnopyranosyloxy)-5β,14β-card-20(22)-enolide.

5. A compound as in claim 1 which is 3-ethinyl-14-hydroxy-3α-(α-L-rhamnopyranosyloxy)-5β,14β-card-20(22)-enolide.

6. A compound as in claim 1 which is 3β-(β-D-glucopyranosyloxy)-14-hydroxy-3-methyl-5β,14β-card-20(22)-enolide.

7. A method for making compounds as in claim 1 which comprises reacting, in the presence of an acid acceptor, an aglycone of the formula

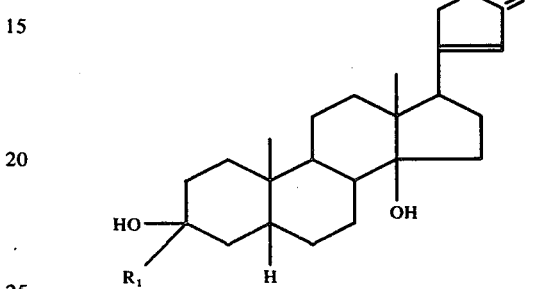

wherein $R_1$ has the same meaning as in claim 1, with an acylated 1-halo-hexopyranose of the formula

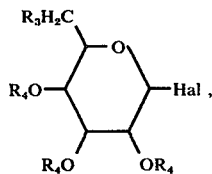

wherein Hal is halogen, $R_3$ is hydrogen or alkanoyloxy having 1 – 4 carbon atoms, and $R_4$ is alkanoyl having 1 – 4 carbon atoms or benzoyl, and subsequently cleaving the acyl groups.

8. A pharmaceutical composition containing a cardioactively effective amount of a compound as in claim 1 as an active ingredient, in combination with a pharmaceutical excipient.

* * * * *